(12) United States Patent
Fox et al.

(10) Patent No.: US 10,955,150 B2
(45) Date of Patent: Mar. 23, 2021

(54) ROOM AIR PURIFIER WITH RFID READER

(71) Applicant: 3M INNOVATIVE PROPERTIES COMPANY, St. Paul, MN (US)

(72) Inventors: Andrew R. Fox, Oakdale, MN (US); Liang Cheng, Shanghai (CN); Weilai Jiang, Woodbury, MN (US); Yinghua Yang, Shanghai (CN); Zhijun Yang, Shanghai (CN); Jie Zhou, Shanghai (CN); Yixiong Chen, Shanghai (CN); Xiaodan Chen, Shenzhen (CN); Pan Liu, Shenzhen (CN); Ling Chen, Shanghai (CN); Wenqian Tang, Shanghai (CN); Liliang Liu, Shanghai (CN)

(73) Assignee: SM Innovative Properties Company, St. Paul, MN (US)

( * ) Notice: Subject to any disclaimer, the term of this patent is extended or adjusted under 35 U.S.C. 154(b) by 203 days.

(21) Appl. No.: 16/087,453

(22) PCT Filed: Mar. 24, 2016

(86) PCT No.: PCT/CN2016/077210
§ 371 (c)(1),
(2) Date: Sep. 21, 2018

(87) PCT Pub. No.: WO2017/161530
PCT Pub. Date: Sep. 28, 2017

(65) Prior Publication Data
US 2019/0107302 A1 Apr. 11, 2019

(51) Int. Cl.
*F24F 3/00* (2006.01)
*F24F 3/16* (2021.01)
(Continued)

(52) U.S. Cl.
CPC ............. *F24F 3/1603* (2013.01); *A61L 9/00* (2013.01); *B01D 46/0086* (2013.01);
(Continued)

(58) Field of Classification Search
CPC ........ F24F 3/1603; F24F 2110/50; F24F 3/16; F24F 11/56; B01D 46/10; B01D 46/429; B01D 46/12; B01D 23/00
See application file for complete search history.

(56) References Cited

U.S. PATENT DOCUMENTS

| 4,588,537 A | 5/1986 | Klaase |
| 4,798,850 A | 1/1989 | Brown |

(Continued)

FOREIGN PATENT DOCUMENTS

| CN | 201603482 | 10/2010 |
| CN | 201612874 | 10/2010 |

(Continued)

OTHER PUBLICATIONS

International Search report for PCT International Application No. PCT/CN2016/077210 dated Dec. 8, 2016, 5 pages.

*Primary Examiner* — Sharon Pregler
(74) *Attorney, Agent, or Firm* — Kenneth B. Wood

(57) ABSTRACT

A room air purifier comprises housing (9), air filter (100), RFID reader (143), RFID tag (120), and a wireless communication unit (142). A method is how to operating the room air purifier.

14 Claims, 5 Drawing Sheets

(51) Int. Cl.

| | | |
|---|---|---|
| *F24F 11/56* | (2018.01) | |
| *A61L 9/00* | (2006.01) | |
| *F24F 3/044* | (2006.01) | |
| *F24F 1/02* | (2019.01) | |
| *H04W 4/80* | (2018.01) | |
| *B01D 46/00* | (2006.01) | |
| *B01D 46/42* | (2006.01) | |

(52) U.S. Cl.
CPC .............. *B01D 46/429* (2013.01); *F24F 1/02* (2013.01); *F24F 3/044* (2013.01); *F24F 3/16* (2013.01); *F24F 11/56* (2018.01); *H04W 4/80* (2018.02); *B01D 2279/50* (2013.01)

(56) References Cited

U.S. PATENT DOCUMENTS

| | | | |
|---|---|---|---|
| 5,496,507 A | 3/1996 | Angadjivand | |
| 5,914,453 A | 6/1999 | James | |
| 6,447,587 B1 | 9/2002 | Pillion | |
| 6,508,868 B2 | 1/2003 | Pillion | |
| 6,711,524 B2 | 3/2004 | Wolf | |
| 7,947,142 B2 | 5/2011 | Fox | |
| 8,007,568 B2 | 8/2011 | DiLeo | |
| 8,242,893 B1 | 8/2012 | Lin | |
| 8,419,817 B2 | 4/2013 | Sundet | |
| 9,737,842 B2 * | 8/2017 | Matlin | B01D 46/448 |
| 2005/0060974 A1 | 3/2005 | Palmerton | |
| 2006/0265149 A1 | 11/2006 | Palmerton | |
| 2007/0012181 A1 | 1/2007 | Niezgoda | |
| 2007/0221061 A1 | 9/2007 | Steiner | |
| 2008/0087588 A1 | 4/2008 | Grzonka | |
| 2009/0293279 A1 | 12/2009 | Sebastian | |
| 2012/0151889 A1 | 6/2012 | Horey et al. | |
| 2013/0220900 A1 | 8/2013 | Milvert | |
| 2014/0306797 A1 | 10/2014 | Cornell | |
| 2015/0101669 A1 | 4/2015 | Krause | |
| 2015/0306533 A1 | 10/2015 | Matlin | |
| 2015/0338311 A1 | 11/2015 | Marek | |
| 2016/0001102 A1 * | 1/2016 | Huh | A62B 18/02 128/206.17 |
| 2017/0341001 A1 | 11/2017 | Jousma et al. | |
| 2018/0161716 A1 | 6/2018 | Li | |

FOREIGN PATENT DOCUMENTS

| | | |
|---|---|---|
| CN | 102486823 | 6/2012 |
| CN | 202270419 | 6/2012 |
| CN | 202962103 | 6/2013 |
| CN | 204365053 | 6/2015 |
| CN | 104801099 | 7/2015 |
| EP | 1985351 | 10/2008 |
| FR | 2898964 | 9/2007 |
| FR | 2951653 | 10/2008 |
| GB | 2416306 | 1/2006 |
| KR | 100851616 | 8/2008 |
| WO | WO 2005-113112 | 12/2005 |
| WO | WO 2006-055295 | 5/2006 |
| WO | WO 2006-114517 | 11/2006 |
| WO | WO 2014-008040 | 1/2014 |
| WO | WO 2015-057956 | 4/2015 |
| WO | WO 2015-171571 | 11/2015 |
| WO | WO 2017-106434 | 6/2017 |

* cited by examiner

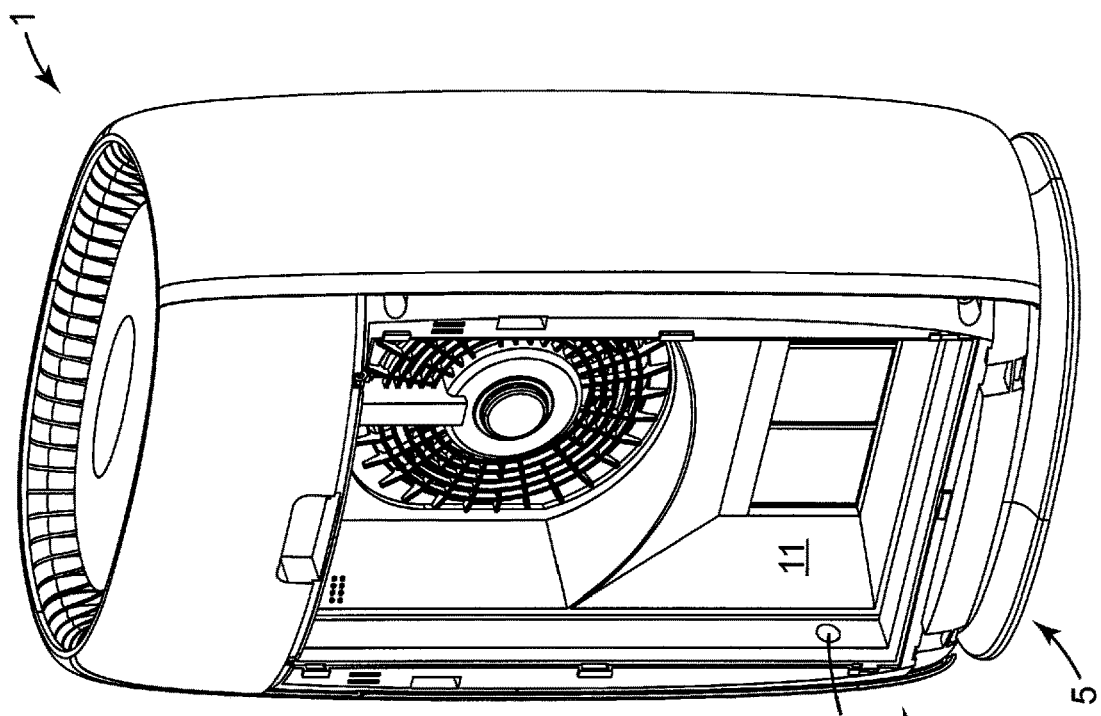
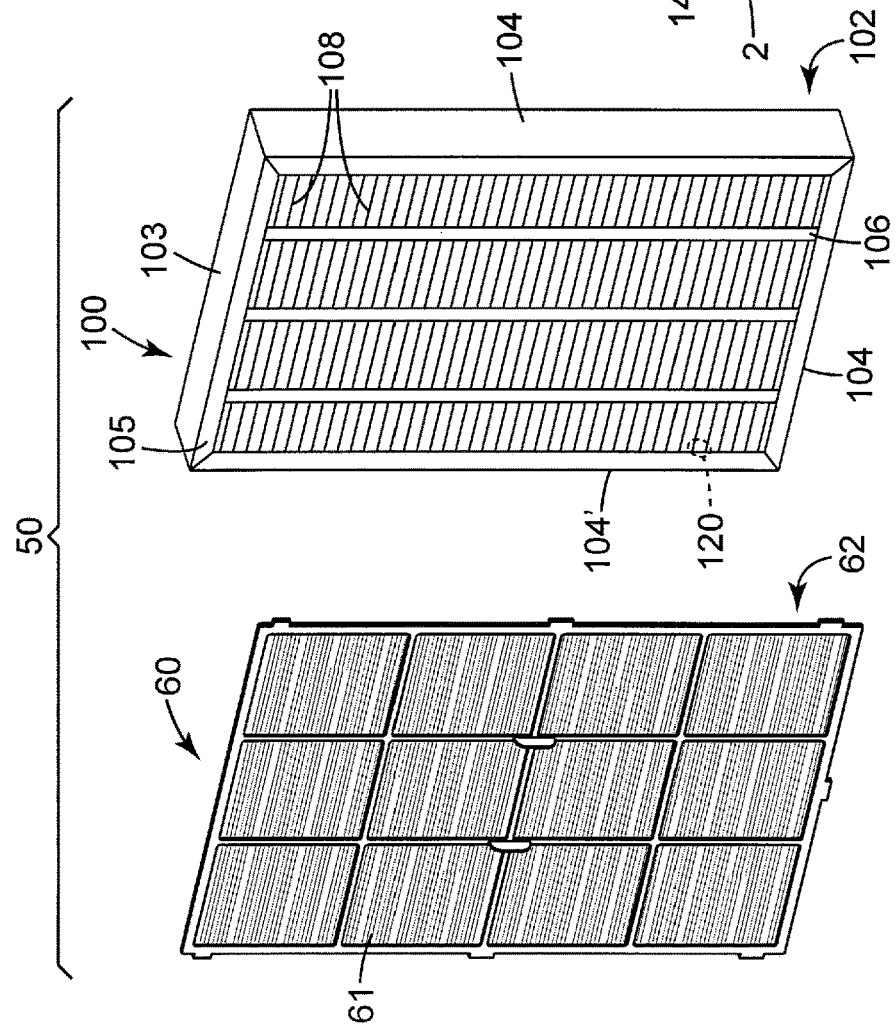
Fig. 3

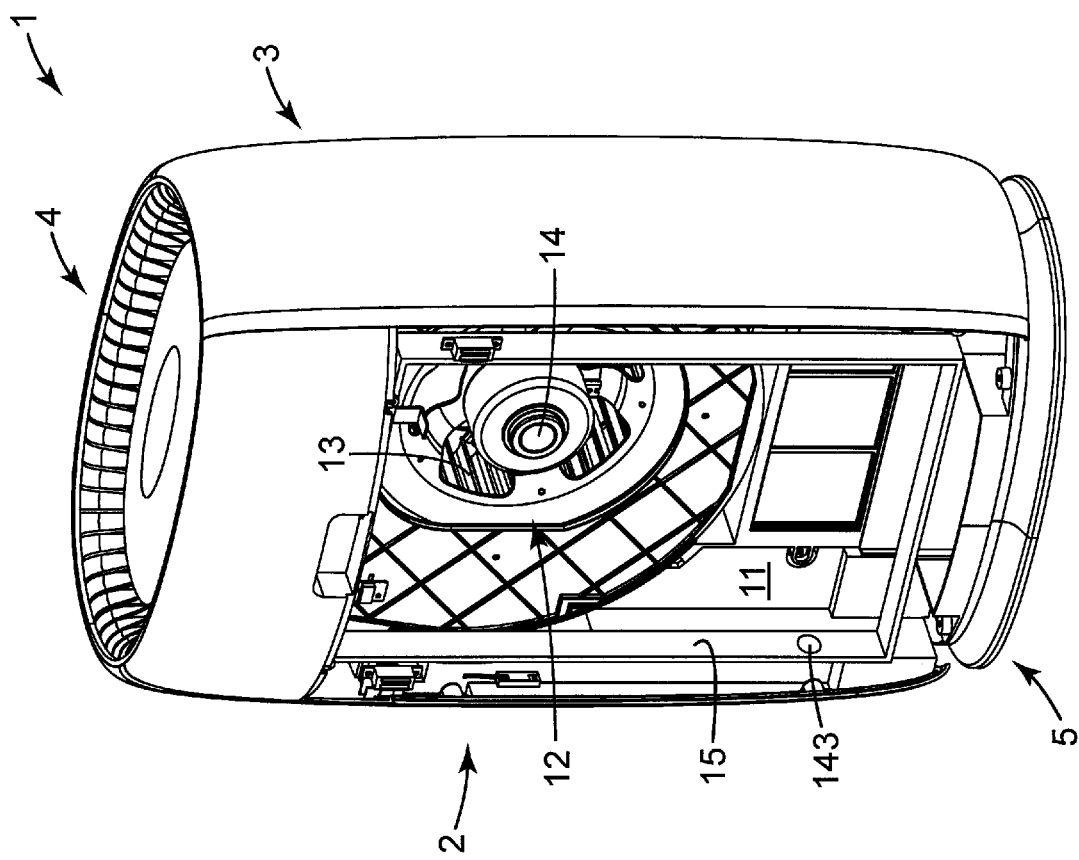
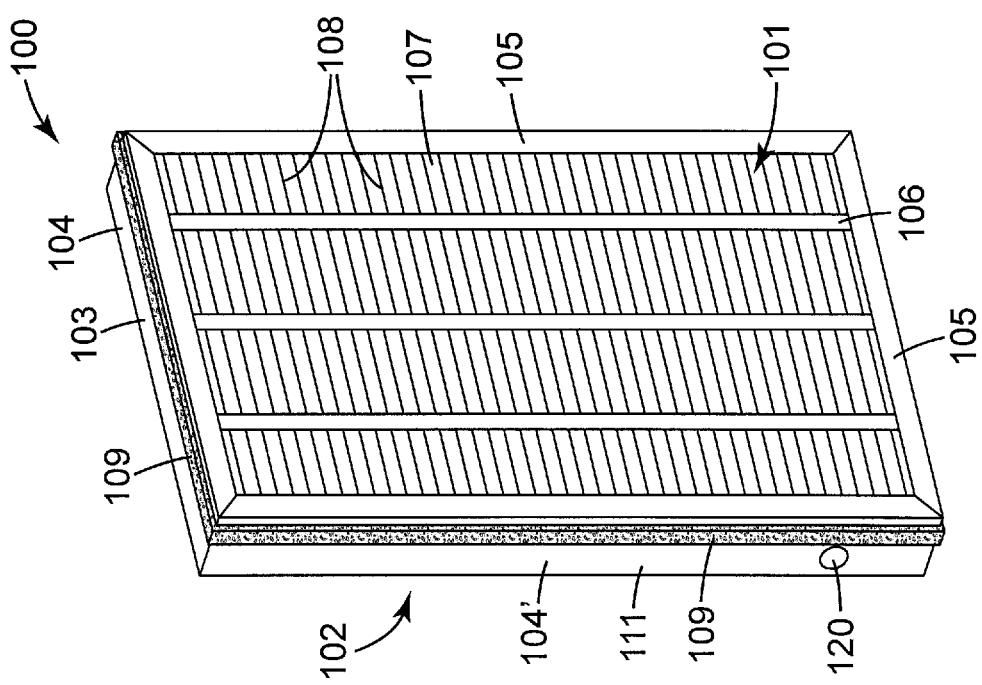

ROOM AIR PURIFIER WITH RFID READER

BACKGROUND

Room air purifiers are often used to purify (e.g., to remove at least some fine particles from) ambient air e.g. in rooms of houses, condominiums, apartments, offices, and so on.

SUMMARY

In broad summary, herein is disclosed a room air purifier comprising an RFID reader and a wireless communication unit, and methods of using such a room air purifier. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

BRIEF DESCRIPTION OF THE DRAWINGS

FIG. 3 is a front-side perspective partially exploded view of an exemplary room air purifier with a front cover panel omitted and with an air filter assembly shown in exploded view.

FIG. 4 is a front-side perspective view of an exemplary disposable air filter as disclosed herein.

FIG. 5 is a front-side perspective view of an exemplary room air purifier as disclosed herein, with a front cover panel, air filter assembly, and other internal components omitted to show an electric motor-driven fan of the room air purifier.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. As used herein, the term "front" refers to a major side of the room air purifier that comprises an air inlet; "rear" refers to the opposite side of the room air purifier. However, these terms are used purely for convenience of description and have no limiting meaning with regard to how a room air purifier is positioned or oriented within a room. Similarly, "bottom" or "lower" end refers to the end of a room air purifier that is lowermost in ordinary operation of the room air purifier and that may be configured to rest on a floor or other horizontal surface. However, noting that in some instances a room air purifier may be e.g. attached to a wall rather than e.g. resting on a floor, this term is likewise not limiting. The terms "upstream" and "downstream" are defined with respect to the direction of airflow through the disposable air filter.

DETAILED DESCRIPTION

Figure 1:
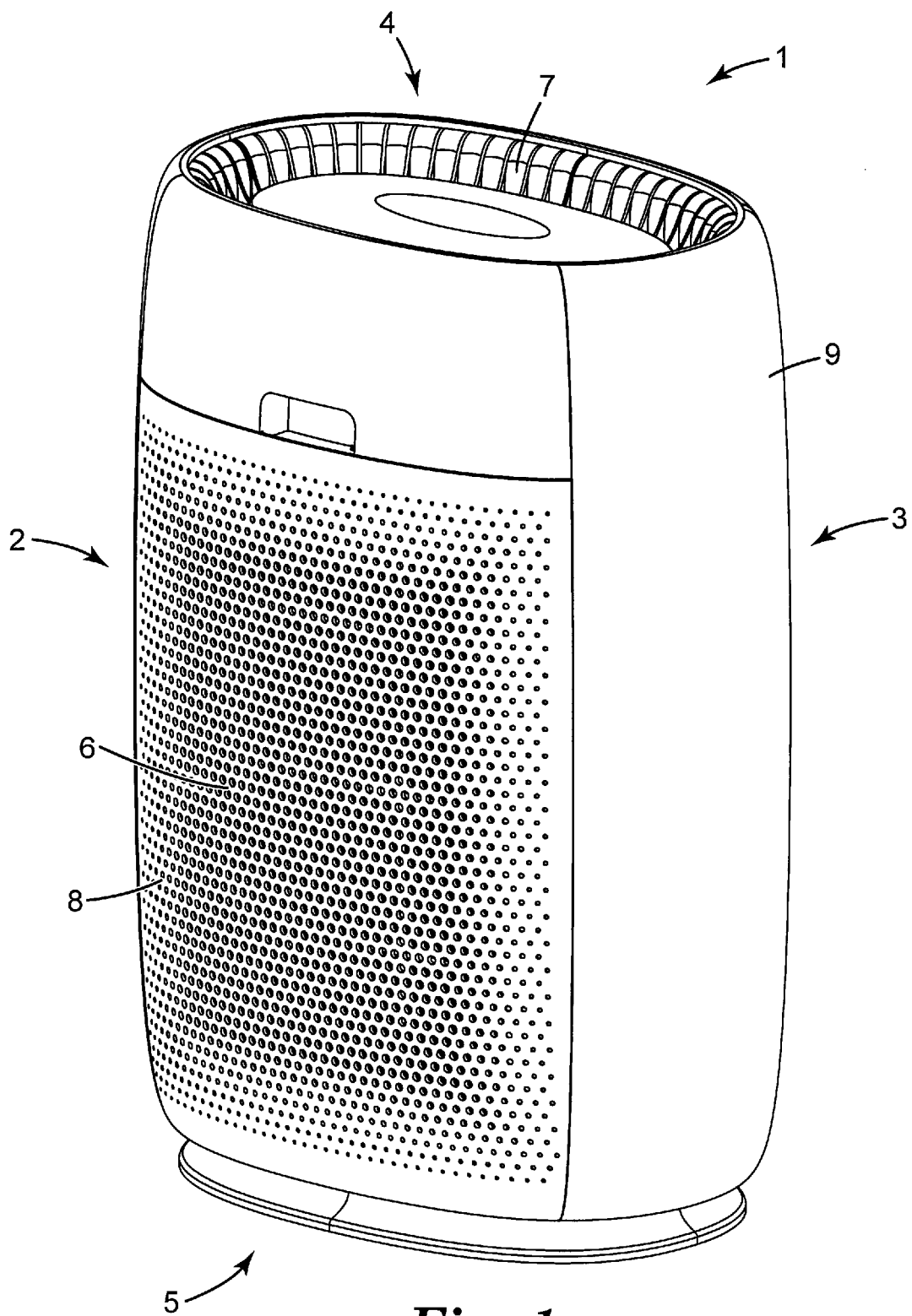
FIG. 1 is a front-side perspective view of an exemplary room air purifier as disclosed herein.

Shown in FIG. 1 in front-side perspective view is an exemplary room air purifier 1. Room air purifier 1 includes a housing 9 defining an air inlet 6, an air outlet 7 and an airflow path therebetween. Housing 9 may also establish a "front" side 2, a "rear" side 3, and top 4 and bottom 5 of the room air purifier. Often, housing 9 may be constructed of one or more molded polymeric parts that are assembled together to form a hollow interior defining the airflow path therethrough as well as providing spaces for components such as motors, control units, and so on. However, in general, housing 9 and parts thereof may be made of any suitable material. Air inlet 6 may be provided at any suitable location; often, it may be conveniently located on a major side of the room air purifier. In at least some embodiments, air inlet 6 may be provided by way of one or more through-apertures in a removable cover panel 8 (e.g., a front cover panel) of room air purifier 1. Cover panel 8 can be removed (as in the view of FIG. 2) to allow access to air filter receptacle 11 into which at least one disposable air filter 100 can be installed. (In some embodiments, air filter 100 may be insertable into receptacle 11 through a slot in the top, bottom, or lateral side of the room air purifier.) Room air purifier 1 includes at least one fan 12 that motivates (e.g., pulls) air through the filter media of the disposable air filter and that expels the filtered air through air outlet 7. Air outlet 7 may be provided e.g. by any suitable number of through-apertures in housing 9. In the illustrated embodiment air outlet 7 is located at the top (upper) end of the room air purifier; however, air outlet 7 can be at any suitable location.

Room air purifier 1 is configured to receive at least one disposable air filter 100 into air filter receptacle 11 thereof. In at least some embodiments, a disposable air filter 100 may be installed into room air purifier 1 as part of an air filter assembly 50, which assembly may include a prefilter 60 in addition to at least one disposable air filter 100 (as exemplified in FIG. 3). If present, prefilter 60 may comprise an upstream face 61 that faces toward the incoming airflow and a downstream face 62 that faces toward (and may often be in at least partial contact with) upstream face 101 of a disposable filter 100.

A disposable air filter 100 (and prefilter 60 if present) may often exhibit a generally rectangular shape (which includes square shapes). Disposable filter 100 may comprise an upstream face 101 and a downstream face 102, and may comprise a filter media 107 surrounded by a perimeter frame 103, as shown in exemplary embodiment in FIGS. 3 and 4. In various embodiments, filter media 107 may be pleated (e.g. as in FIGS. 3 and 4) so as to exhibit readily identifiable pleats 108; or, it may be unpleated. Perimeter frame 103 may often comprise sidewalls (e.g., top, bottom, left and right sidewalls) 104 that define terminal edges of the framed filter. Frame 103 may often further comprise flanges 105 that extend from sidewalls 104 for a short distance toward the center of the filter media, and that may be present on the downstream face 102 and/or the upstream face 101 of the filter 100. Upstream and downstream frame flanges may be generally parallel to each other (e.g., in the case of a U-shaped or "channel" frame); or, one set of flanges may be angled so as to form a so-called "pinch" frame. A frame 103 may be made of any suitable material(s), e.g. paperboard or cardboard that is folded to provide the various sidewalls and flanges. In some embodiments, a frame 103 may be made of an injection molded plastic material. In some embodiments, at least the downstream face 102 of filter 100 may comprise support members (exemplary support members 106 are visible in FIG. 3) that extend at least partially across filter media 107 (in any direction). Such members may provide additional support, particularly on the downstream side of the filter media; and (particularly for pleated filter media), such members may assist in minimizing any deformation of the filter media in response to air pressure during operation of the room air purifier. In some embodiments such members may be strips of paperboard that may be connected to frame 103 at their terminal ends. In other embodiments such members may be lengths of adhesive strands (e.g., of the general type described in U.S. Pat. No. 8,419,817 to Sundet). If the filter media is pleated, any such adhesive strands may be deposited either before or after the filter media is pleated.

The filter media 107 (whether pleated or not) of a disposable air filter 100 may be comprised of nearly any material, in any configuration, that is capable of filtering moving air. Such media may include, but is not limited to, fibrous materials (e.g., nonwoven webs, fiberglass webs, and so on), honeycomb structures loaded with filter media and/or sorbent material, and so on. In particular embodiments, the filter media may include at least one layer that comprises at least some material that can be electrically charged to form an electret material. In particular embodiments, the filter media may be a multilayer media that comprises at least one layer that includes an electret material, and at least one layer that includes a sorbent material. In some embodiments filter media 107 may comprise at least one layer capable of HEPA filtration.

If at least one layer of filter media 107 is to be charged, this may be done by any suitable method, for example, by imparting electric charge to the nonwoven web using water as taught in U.S. Pat. No. 5,496,507 to Angadjivand, or as taught in U.S. Patent Publication No. 2009/0293279 to Sebastian. Nonwoven electret webs may also be produced by corona charging as described in U.S. Pat. No. 4,588,537 to Klaase, or using mechanical approaches to impart an electric charge to fibers as described in U.S. Pat. No. 4,798,850 to Brown. Any combination of such approaches may be used. In various embodiments, filter media 107 may exhibit a % Penetration (using Dioctyl Phthalate as a challenge material, and tested using methods described in U.S. Pat. No. 7,947,142 to Fox) of less than about 50, 40, 30, 20, 10, or 5%.

If at least one layer of the filter media 107 is to exhibit sorbent functionality, any suitable sorbent(s), in any convenient physical form, may be included in such a layer. In particular embodiments, such a sorbent is capable of capturing formaldehyde. In some embodiments, the sorbent includes at least some activated carbon. If desired, the activated carbon may be treated to enhance its ability to capture formaldehyde. Suitable treatments may e.g. provide the activated carbon with at least some amine functionality and/or at least some manganate functionality and/or at least some iodide functionality. Specific examples of treated activated carbons that may be suitable include those that have been treated with e.g. potassium permanganate, urea, urea/phosphoric acid, and/or potassium iodide. Other sorbents that may be potentially suitable e.g. for removing formaldehyde include e.g. treated zeolites and treated activated alumina. Such materials may be included e.g. along with treated activated carbon if desired. In particular embodiments, the sorbent may include materials described in U.S. Provisional Patent Application No. 62/269,613 to Wendland, entitled Polymeric Sorbents for Aldehydes, which is incorporated by reference in its entirety herein.

The one or more sorbents may be provided in any usable form; for example as particles, which may be e.g. powder, beads, flakes, whiskers, granules or agglomerates. The sorbent particle size may vary as desired. The sorbent particles may be incorporated into or onto a layer of filter media 107 in any desired fashion. For example, in various embodiments the sorbent particles may be physically entangled with fibers of a layer of filter media 107, may be adhesively bonded to such fibers, or some combination of both mechanisms may be used.

Prefilter 60, if present, can be of any suitable design, made of any suitable material. In some embodiments, prefilter 60 may serve as coarse prefilter that captures large particles of dirt, hair, and the like but that allows fine particles to pass therethrough e.g. to be captured by the filter media 107 of disposable filter 100. In some embodiments, prefilter 60 may be a molded plastic item (e.g., made of a thermoplastic polymer such as an injection-moldable resin). If prefilter 60 comprises a perimeter frame, the perimeter frame may be integral with the molded material that makes up the rest of the prefilter; or, a separate frame can be used and can have e.g. any suitable netting, scrim, or the like attached thereto in order to form the prefilter.

In some embodiments, prefilter 60 may be reusable and washable (rather than being a single-use, disposable item). In such embodiments, prefilter 60 may be supplied separately from disposable filter 100 rather than being supplied along with (e.g., permanently attached to) disposable filter. In some embodiments, when a prefilter 60 is installed in room air purifier 1 (e.g., as part of a filter assembly 50 including disposable air filter 100), prefilter 60 may be sandwiched in between disposable filter 100 and cover panel 8 of the room air purifier. In other embodiments, a cover panel 8 of room air purifier 1 may itself be configured (e.g. by choice of the number and size of through-apertures therein) to function as a prefilter. In some embodiments, when disposable filter 100 and prefilter 60 are installed in room air purifier 1, downstream face 62 of prefilter 60 may rest against upstream face 101 of disposable filter 100 (e.g., it may be pressed thereagainst by a force applied by cover panel 8). In other embodiments, prefilter 60 may be temporarily attached to disposable filter 100 in some manner (e.g., by way of complementary attachment features provided on a frame of the prefilter and on a frame of the disposable filter). In still other embodiments, prefilter 60, when installed, may be attached to room air purifier 1 itself (e.g. it may be attached to attachment points located with filter receptacle 11 of room air purifier 1).

In some embodiments, more than one disposable air filter 100 may be used in room air purifier 1. For example, two (or more) such disposable air filters 100 may be placed within an air filter receptacle 11 so that one filter is located downstream of the other filter. By way of a specific example, an upstream disposable air filter might be configured to capture fine particles and a downstream air filter might be configured to capture one or more gases/vapors, e.g. formaldehyde, carbon monoxide, etc. Two such filters may be installed separately into air filter receptacle 11; or they may be assembled (and e.g. attached to each other) into a filter assembly 50 before being installed into air filter receptacle 11. In either case, an optional prefilter 60 may also be used if desired. If two (or more) such disposable air filters are used, either or both of the air filters may include an RFID tag as described below.

At least one disposable air filter 100 will comprise at least one RFID (radiofrequency identification) tag 120, as indicated in FIG. 3 and as visible in the view of FIG. 4. In some embodiments, an RFID tag 120 may be mounted to any portion of a perimeter frame 103 of air filter 100. For example, an RFID tag 120 may be mounted to an interior major surface of a sidewall of the frame, or to an exterior or interior (i.e., visible or not visible) major surface of an upstream or downstream flange of the frame. In some embodiments, RFID tag 120 is mounted to (e.g., attached to, e.g. adhesively attached to) an major outward surface of a sidewall 104 of perimeter frame 103 of disposable air filter 100. (In the Figures, the nomenclature of 104' is used to identify a particular sidewall 104 to which an RFID tag is attached.) RFID tag 120 may be any suitable RFID tag. In many embodiments, RFID tag 120 may be a passive tag, meaning that it does not include any kind of power source and is solely powered by the electromagnetic energy that is impinged upon it by the RFID reader. In some embodiments, RFID tag 120 may be a conventional RFID tag (operating e.g. at high, medium or low frequency) whose range is not particularly limited. In particular embodiments, RFID tag 120 may be a so-called Near Field Communication (NFC) tag, which will be recognized by the skilled person as being a particular type of RFID tag that operates (e.g. at 13.56 MHz) only over the range of a few (e.g., ten or less) centimeters. In some embodiments RFID tag 120 is a readable (only) tag; in other embodiments it may be a readable/writeable tag as discussed in detail later herein. In some embodiments, RFID tag 120 may conveniently be supplied with an adhesive backing so that RFID tag 120 can be quickly and easily installed onto a surface (e.g., major outward surface 111 as shown in FIG. 4) of a sidewall 104' of a frame of filter 100.

In some embodiments, disposable air filter 100 may comprise at least one strip 109 of resilient material that is located on, and extends along at least a portion of the longest dimension of, the particular sidewall 104' on which RFID tag 120 is mounted. In particular embodiments, similar strips 109 are located on, and extend along at least a portion of, one or more of the other sidewalls (e.g., the left, right, top or bottom sidewalls) of frame 103 (as shown in exemplary embodiment in FIG. 4). It will be appreciated that the presence of this resilient material may protect RFID tag 120 from being dislodged, or scraped or otherwise damaged, during the act of inserting disposable filter 100 into the air filter receptacle 11 of room air purifier 1. Moreover (particularly if strips 109 of resilient material are present on at least two oppositely-facing sidewalls, or are present on all four sidewalls, of frame 103), these strips may improve the snugness with which filter 100 can be installed in receptacle 11 and may minimize any air leaks around the perimeter of the installed filter.

Such strips of resilient material may have any suitable composition and form. A particularly convenient arrangement may to use an adhesive-backed foam strip that can be adhesively attached to a surface of a sidewall of the filter frame. The foam may be of any suitable composition and structure (e.g., open-celled, closed-cell, etc.) that provides the desired resiliency and cushioning. The thickness of the resilient material of the strip can be of any desired value; however, it may be particularly useful if the resilient material exhibits a thickness that is significantly greater than the thickness of the RFID tag, in order to most effectively protect the RFID tag from damage. In various embodiments, the (uncompressed) thickness of the resilient material can be greater than the thickness of the RFID tag by a factor of about 2, 4, 6, 8, 10, 12, 14, or 20.

In various embodiments, a strip of resilient material may extend along at least about 50, 60, 70, 80, 90, or 95% of the length of a sidewall to which the strip is attached. (While shorter lengths of resilient material may still help to protect the RFID tag as long as they are positioned suitably close to the RFID tag, any effect on e.g. minimizing air leaks around the perimeter of the framed filter may be most pronounced when the strip of resilient material extends along most or all of the length of each sidewall.)

In some embodiments, the strip of resilient material may have a width, along the upstream-downstream direction of the sidewall (e.g., the left-right direction of major sidewall 104' as viewed in FIG. 4), that approaches the upstream-downstream extent (width) of the sidewall. In other words, in such embodiments, the strip of resilient material may occupy most or all of the upstream-downstream extent of the sidewall. In such cases, the strip of resilient material may be applied directly atop the RFID tag, so that the RFID tag is sandwiched between the strip of resilient material and the sidewall of the frame. As long as the strip of resilient material does not unduly interfere with the transmission of RFID signals therethrough, such an arrangement may be satisfactory. In other arrangements, a strip of resilient material may only occupy a portion of the upstream-downstream extent of the sidewall. In such cases, the RFID tag may be adjacent to the strip of resilient material (rather than covered by the strip of material), as shown in exemplary embodiment in FIG. 4. Arrangements such as this may advantageously allow the RFID tag to be visible and may aid a user in correctly orienting the air filter when it is installed into the receptacle of the room air purifier.

Figure 2:
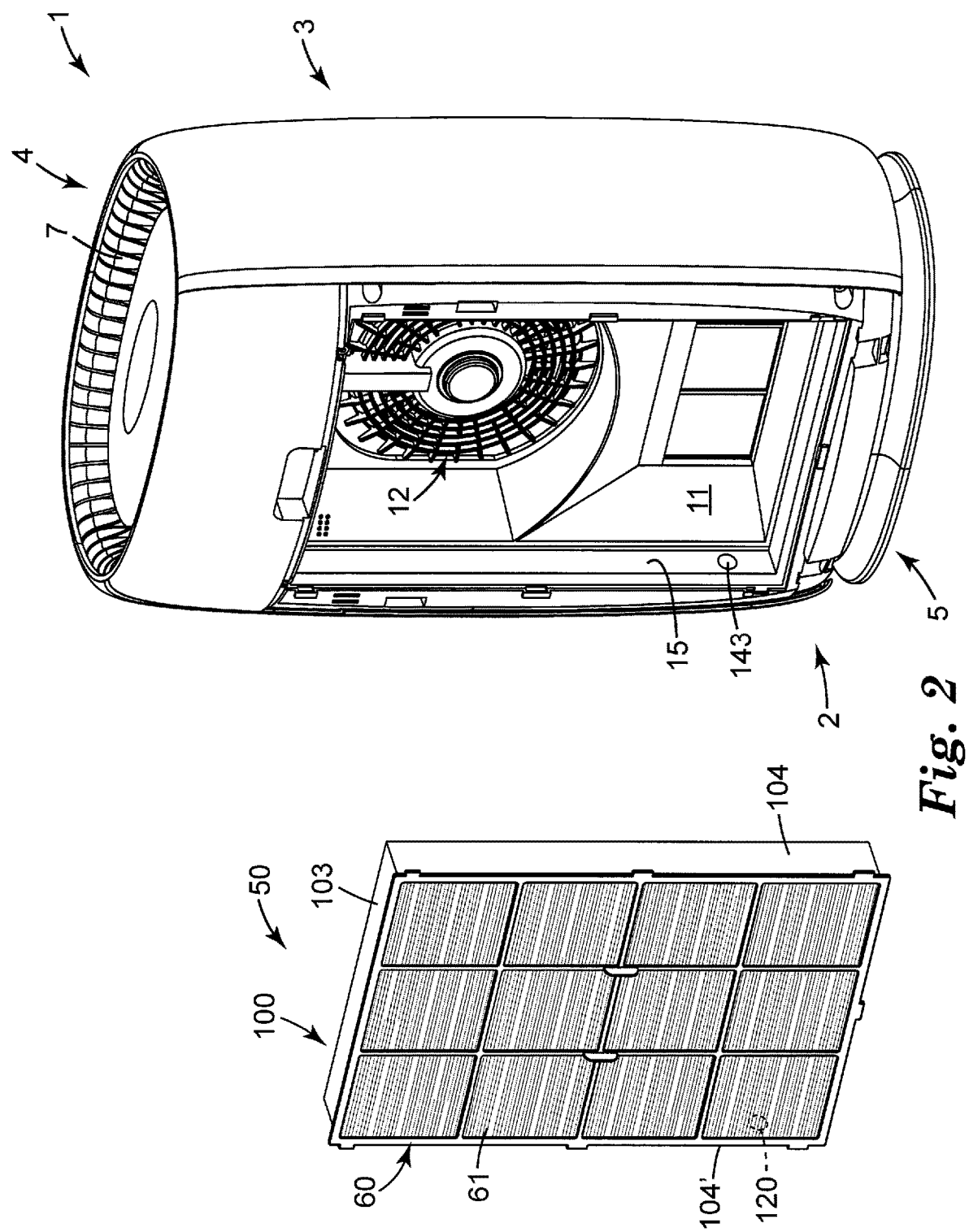
FIG. 2 is a front-side perspective partially exploded view of an exemplary room air purifier with a front cover panel omitted to show an exemplary air filter assembly.

Room air purifier 1 comprises a fan 12 (partially visible in the views of FIGS. 2 and 3). In the view of FIG. 5, various components have been omitted so that electric motor 14 and impeller 13 of fan 12 are visible. Impeller 13 can be of any suitable type, e.g. a squirrel-cage impeller as shown in FIG. 5. Electric motor 14 can be of any suitable type, e.g. a DC or AC motor of the type often used in room air purifiers. Motor 14 can comprise one or more of rotors, stators, windings, and so on, as is well known. Motor 14 will often be powered by an external source (e.g. by way of a power cord); however, in some embodiments room air purifier 1 may include an internal power source (e.g. a rechargeable battery).

Figure 6:
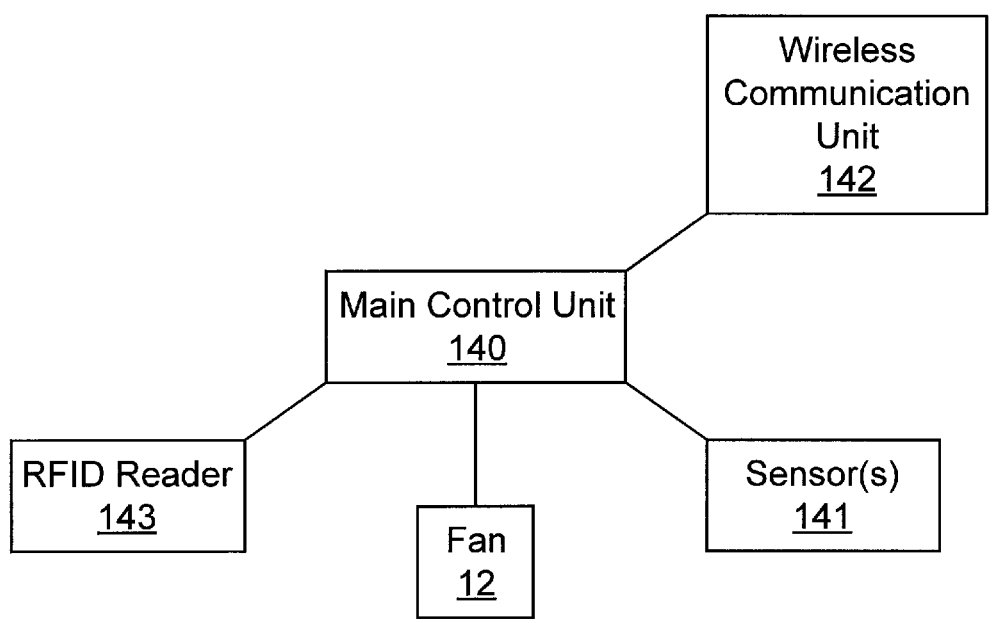
FIG. 6 is a block diagram illustrating exemplary components of a room air purifier.

Room air purifier 1 will comprise a main control unit 140 as signified in the block diagram of FIG. 6. Main control unit 140 may include one or more of printed circuit boards and the like, along with whatever ancillary electrical components are needed. Main control unit 140 is in operative connection with fan 12 (e.g. so that fan 12 can be turned on and off and operated at different fan speeds if desired), and is also in operative connection with various controls and switches, monitors, displays and/or indicators, etc., that are provided on or within housing 9 and that allow a user to directly operate room air purifier 1 (e.g., to turn it off or on, to turn the fan speed up or down, etc.). Main control unit 140 will also be in operative connection (e.g. by hard-wire or fiber-optic connection) with wireless communication unit 142 which allows the main control unit to communicate with an external device. Such arrangements can allow the room air purifier to be operated (and its operating status monitored) remotely, by way of signals sent back and forth between the external device and the main control unit of the room air purifier, rather than being operated directly by way of controls located on the room air purifier itself.

Such an external device may be any suitable device capable of receiving signals from wireless communication unit 142 (and capable of transmitting signals and instructions to wireless communication unit 142). In particular embodiments, the external device is a portable device such as a smartphone, a tablet computer, or a laptop computer.

Such embodiments specifically exclude the external device being any device that is configured and installed to be non-portable (e.g. a dedicated desktop computer, a terminal, a mainframe, a server and so on). Wireless communication unit 142 may be of any suitable type. In various embodiments, it may communicate with the external device, directly or indirectly, via short-range UHF radiowaves (e.g., via the well-known Bluetooth protocol operating in the ISM band from 2.4 to 2.485 GHz), by communication over a Wi-Fi network (whether e.g. locally by way of one or more local routers, via the internet by way of one or more network access points and/or internet routers or servers, or by any combination of these), by communication over a cellular telephone network, by infrared communication, or by any combination of these. Main control unit 140 will also be in operative connection (which may be conveniently provided by a hard-wire or fiber-optic connection, but could be a wireless connection) with RFID reader 143, as discussed in further detail later herein.

In some embodiments, main control unit 140 is also in operative connection with one or more sensors 141. Such sensors may sense or detect, e.g. quantitatively or semi-quantitatively, any item, parameter, or analyte of interest. In some embodiments, a sensor 141 may be a particle detector; in specific embodiments, sensor 141 may be configured to detect fine particles that have a diameter of 2.5 μm or less (particles of this size are often referred to as $PM_{2.5}$ particles). Such particles (regardless of size) may be e.g. solid particles, dust, aerosol, and so on. In some embodiments, a particle sensor may be an optical sensor that operates e.g. by way of one or more laser beams. However, in general the fine sensor may be any sensor that is able to sense particulates, dust or the like in air, by any suitable mechanism. One example of a potentially suitable fine particle sensor is the product available as Model No. PPD4NS from Shinyei Technology (Kobe, Japan). In some embodiments, a sensor 141 may be a volatile organic chemical (VOC) detector, operating by any suitable mechanism.

Regardless of the particular item that is being sensed, in at least some embodiments sensor or sensors 141 are positioned upstream of disposable filter 100 (e.g., upstream of filter assembly 50) so as to monitor upstream air rather than monitoring downstream air that has already passed through the filter media 107 of disposable filter 100. Such positioning allows the sensors to track the level of the desired item(s) in the ambient atmosphere over time. Sensor(s) 141 may accordingly be positioned within filter receptacle 11, in a position upstream of filter 100. Alternatively, one or more sensors 141 may be positioned on an external surface of housing 9 (although they may be covered e.g. by a louver, deflector, shield, etc., that allows ambient air to reach the sensor but protects the sensor from impact damage and from splashes of liquid). Any arrangement will suffice as long as it allows the sensor(s) to monitor the ambient atmosphere in the desired manner.

As noted, room air purifier 1 comprises at least one RFID reader 143 that is in operative connection with main control unit 140. RFID reader 143 is configured to read information from (and, optionally, to write information to) RFID tag 120 of disposable filter 100. It will be appreciated that the type and characteristics of RFID reader 143 of the room air purifier, and the type and characteristics of the aforementioned RFID tag 120, will be chosen in tandem. For example, if RFID tag 120 is an NFC tag, then RFID reader 143 will be an NFC reader; if RFID tag 120 is a readable/writeable tag, then RFID reader 143 should be capable of writing information onto tag 120 in addition to reading information from tag 120.

In some embodiments, e.g. in which RFID reader 143 and tag 120 are conventional RFID devices with relatively long range capability, it may not be important that reader 143 and tag 120 are in close physical proximity to each other when disposable filter 100 is installed in room air purifier 1. However, in other embodiments RFID reader 143 and tag 120 may be relatively limited-range devices. For example, as noted previously, they may be so-called Near-Field Communication devices, which the skilled person will recognize as being a particular type of RFID communication performed over very limited ranges, e.g. 10 cm or less. Accordingly, in at least some embodiments, RFID reader 143 may be located in a position within filter receptacle 11 of room air purifier 1, to which RFID tag 120 of disposable filter 100 will be placed in very close proximity (in various embodiments, within 8, 6, 5, 4, 3, 2 or 1 cm, at the point of closest approach) when filter 100 is installed in purifier 1.

An exemplary arrangement of this type is depicted in FIG. 3, in which RFID reader 143 is positioned on inner lateral wall 15 of filter receptacle 11, so that RFID tag 120 (which is not directly visible in the view of FIG. 3, but is visible in the view of FIG. 4) of filter 100 will be placed in very close proximity to (e.g., within about 2 cm of) to reader 143 when filter 100 is properly installed in receptacle 11. Filter 100 and/or some portion of room air purifier 1 may include indicia, diagrams, or instructions of any suitable sort, to guide the user in properly orienting filter 100 when inserting it into receptacle 11 so that RFID tag 120 is positioned properly. In some embodiments, filter 100 may comprise one or more registration features (e.g., a notched or angled corner of the frame, a cavity or detent structure, etc.) that mate with a complementary registration feature of receptacle 11 when filter 100 is properly installed.

In some embodiments, RFID reader 143 may be mounted on an inward-facing wall of housing 9 that defines filter receptacle 11, so that in operation of RFID reader 143, there may be nothing but air (or possibly a portion of the above-described strip of resilient material) in the space between RFID reader 143 and RFID tag 120. In other embodiments, RFID reader 143 may be positioned behind a wall that defines filter receptacle 11, so that the RFID reading takes place through the wall itself. This may not unacceptably affect the ability to perform the RFID reading, e.g. as long as the wall is thin enough, is made of e.g. molded plastic rather than metal, and so on.

If two disposable air filters 100 are used, each bearing an RFID tag 120, room air purifier 1 may be provided with two RFID readers 143. Or, a single RFID reader may be used that is capable of interrogating two (or more) RFID tags e.g. on separate disposable air filters.

Room air purifiers often use motors (e.g. DC motors) that may operate at a fairly high voltage (e.g., in the range of 300 V). Such motors may generate a significant electromagnetic fields (EMF) and thus may produce RF (radiofrequency) signals that may interfere with RFID reading. Accordingly, in at least some embodiments, RFID reader 143 is positioned remotely from motor 14 of room air purifier 1. In this context, positioned remotely is defined as meaning that no part of RFID reader 143 is located within 10 cm of any electromagnetically-active component of motor 14. In this context, electromagnetically-active signifies components such as e.g. rotors, stators, and windings, but does not include e.g. housings, shrouds, gaskets, and so on. In further embodiments, RFID reader 143 is positioned at least about 15, 20, or 25 cm from motor 14. In still further embodiments (and irrespective of the distance between RFID reader 143 and motor 14) one or more EMF shields can be positioned between (i.e., interposed between so as to block any line-of-sight path therebetween) RFID reader 143 and motor 14, so as to protect RFID reader from electromagnetic interference due to motor 14. Such EMF shields will be familiar to the skilled person; any suitable EMF shield(s) may be used, e.g. one or more layers of metal, one or more layers of metallized polymer film, and so on.

Disposable filter 100 (e.g., as part of a filter assembly 50 including a prefilter 60), when installed into filter receptacle 11 of housing 9 of room air purifier 1, is positioned such that when fan 12 is turned on, a majority (e.g., essentially all) of the air that flows through the airflow path in the housing flows through the filter media 107 of the disposable filter for removal of at least some fine particles, dust and/or or other contaminants from the flowing air. When filter 100 is installed into receptacle 11 of room air purifier 1, RFID reader 143 of room air purifier 1 will interrogate RFID tag 120 of filter 100 and will read information therefrom. This information may include e.g. any or all of the following information regarding the filter that was preloaded (e.g., by the manufacturer of the filter) onto the RFID tag: model number; date of manufacture; date of expiration; the filter type, size, etc.; the lifetime rating of the filter; the lot number and/or serial number of the filter; and, authentication information. Such authentication information (whether in the form of an authentication code, or in any other form) can help the user ensure that the disposable air filter is compatible with the room air filter and in particular that it is not a counterfeit product.

In some embodiments (e.g. in which the RFID tag is a readable-only tag), preloaded information may be the only information that is carried by the RFID tag. However, if the RFID tag is a readable/writeable tag (and the RFID reader of the room air purifier is capable of writing to the RFID tag in addition to reading information from the RFID tag), additional information may be written onto the RFID tag during operation of the room air purifier. For example, an estimated remaining lifetime of the disposable filter 100 may be obtained by the main control unit as discussed in detail later herein. In some embodiments, this estimated remaining lifetime may be displayed e.g. on a display panel of the room air purifier. In some embodiments, this estimated remaining lifetime may be communicated wirelessly (by way of wireless communication unit 142) to an external device such as a smartphone. And, in some embodiments, this estimated lifetime may be written onto the RFID tag of the disposable filter itself. In various embodiments, any combination of any or all of these may be carried out.

It will be appreciated that writing the estimated remaining lifetime of the disposable filter onto the RFID tag of a filter itself can have advantages over keeping this information resident in the main control unit of the room air purifier. For example, in the previously-mentioned embodiment in which two disposable air filters (e.g., one primarily for particles, one primarily for gases/vapors) are used in a room air purifier, it may be necessary to temporarily remove a first filter (e.g. an upstream filter) in order to access and remove a second filter (e.g. a downstream filter). (This may be done for example if the usable lifetime of the second filter is not as great as that of the first filter.) Having the estimated remaining lifetime of the first filter be resident on the RFID tag of the first filter can ensure that this information is preserved so that the first filter, when placed back into the room air purifier, is correctly identified as a re-installed filter (with a shorter remaining lifetime than would be present with a new filter) rather than a newly installed filter.

Furthermore, large buildings may have multiple room air purifiers in different rooms. Maintaining the estimated remaining lifetime of each filter resident on the filter itself means that a filter can be removed from one room air purifier and installed into a different room air purifier, which can interrogate the RFID tag of the filter to ascertain the estimated remaining lifetime of that filter. In other words, the estimated remaining lifetime of an air filter can be monitored and tracked irrespective of whether or not the air filter is moved between different room air purifiers, is removed from and later re-installed into the same room air purifier, and so on.

The estimated remaining lifetime of a disposable air filter may be obtained (calculated) using any method that provides a sufficiently reliable estimate. In one simple approach, an estimated remaining lifetime may take into account only the cumulative run time (the total length of time that the room air purifier has been in powered operation with the filter installed therein). In further approaches, the fan speed (which may vary between e.g. high, medium and low settings) at which the room air purifier is operated may be monitored and this information may be combined with the run time to arrive at an estimated remaining lifetime based on the total volume of air processed. In still further approaches, the concentration of fine particles in the ambient air may be monitored (e.g., by a fine particle sensor 141 as mentioned previously) during the time the room air purifier is in powered operation. This information can be combined with the cumulative run time information and/or with the fan speed information. In this manner an estimate of the remaining lifetime of the filter can be obtained that takes into account not only the total amount of air processed but also takes into account the concentration of fine particles present in the processed air. This can allow the estimated remaining filter lifetime to be based on an estimate of the loading of the filter media with fine particles that has occurred.

An estimated remaining filter lifetime can be derived (e.g., calculated by the main control unit) from the cumulative run time, the average fan speed over that run time, and the average concentration of fine particles in the air during that run time, by any sufficiently predictive algorithm. In some embodiments, the algorithm may be a complex algorithm, meaning that the algorithm does not use a simple additive function, or a simple multiplicative function, of the run time, fan speed, and particle concentration.

Irrespective of whether any information is written onto the RFID tag during operation of the room air purifier, at least some information that is read from the RFID tag will be communicated from the room air purifier to an external device by way of the aforementioned wireless communication unit, during operation of the room air purifier. In some embodiments, the information that is communicated to the external device may be "as-is" information from the RFID tag of the air filter. In other words, such information may be communicated to the external device in very similar or even identical form in which it was stored on the RFID tag. Such "as-is" information might be e.g. preloaded information such as model number, date of manufacture, authentication information, and so on. In other embodiments, the information that is communicated to the external device may be slightly, or even substantially, processed or modified (e.g. by the main control unit) before being communicated to the external device. Such processed or modified information still satisfies the criteria that information that is read from the RFID tag is communicated to the external device. And, of course, information that is calculated by the main control unit (e.g., an estimated remaining lifetime of the filter) may be communicated to the external device.

In some embodiments, a disposable air filter 100 may comprise (e.g. in addition to an RFID tag 120), at least one optically interrogatable automatic identification and data capture (AIDC) label. Such a label may carry any suitable information and may take the form of e.g. a Universal Product Code (UPC) barcode or a Quick Response (QR) code (sometimes referred to as a matrix code or a 2-D barcode), as will be familiar to the ordinary artisan. If such an optically interrogatable code is present, it may be e.g. read by a reader installed in the external device, and the information gained therefrom can be communicated to the room air purifier by well-known methods and devices.

LIST OF EXEMPLARY EMBODIMENTS

Embodiment 1 is a room air purifier comprising: a housing defining an air inlet, an air outlet, and an airflow path therethrough, wherein the housing comprises an air filter receptacle that is configured to receive at least one disposable air filter so that a filter medium of the disposable air filter is in the airflow path; an electric motor mounted within the housing and comprising a fan connected thereto, the fan positioned in the airflow path and configured to motivate air to pass through the filter medium of the disposable air filter; at least one RFID reader that is positioned and configured to read an RFID tag that is attached to the at least one disposable air filter, and to communicate information that is read from the RFID tag, to a main control unit of the room air purifier; and, a wireless communication unit that allows the main control unit of the room air purifier to communicate information that is read from the RFID tag by the RFID reader, to an external device.

Embodiment 2 is the room air purifier of embodiment 1 wherein the RFID reader is remotely located from the electric motor of the room air purifier so that the RFID reader is at least 10 cm from the electric motor. Embodiment 3 is the room air purifier of any of embodiments 1-2 wherein the RFID reader is electromagnetically shielded from the electric motor of the room air purifier by at least one EMF shield that is located between the RFID reader and the electric motor.

Embodiment 4 is the room air purifier of any of embodiments 1-3, further comprising at least one disposable air filter removably installed in the air filter receptacle of the housing. Embodiment 5 is the room air purifier of embodiment 4 wherein the disposable air filter is a framed air filter that comprises at least one RFID tag that is mounted on a frame of the disposable air filter. Embodiment 6 is the room air purifier of embodiment 5 wherein the RFID reader of the room air purifier is an RFID reader/writer, and wherein the RFID tag is a readable tag that stores preloaded information regarding the disposable air filter so that the preloaded information can be read by the RFID reader/writer of the room air purifier; and, wherein the RFID tag is a writeable tag that is configured to receive and store information from a main control unit of the room air purifier, by way of the RFID reader/writer.

Embodiment 7 is the room air purifier of any of embodiments 5-6 wherein the RFID tag is mounted on a major outward surface of a sidewall of a frame of the disposable air filter. Embodiment 8 is the room air purifier of embodiment 7 wherein the RFID tag is adhesively attached to a major outward surface of the sidewall of the frame of the disposable air filter.

Embodiment 9 is the room air purifier of any of embodiments 5-8 wherein the framed, disposable air filter further comprises a strip of resilient material that is attached to the major outward surface of the sidewall on which the RFID is mounted, wherein the strip extends along at least about 80% of the elongate length of the sidewall on which the RFID tag is mounted, and wherein the material of the strip protrudes further outward away from the major outward surface of the sidewall than the RFID tag protrudes, by a factor of at least about four. Embodiment 10 is the room air purifier of embodiment 9 wherein the major outward surface of the sidewall exhibits an upstream-downstream extent, wherein the RFID tag occupies a portion of the upstream-downstream extent of the major outward surface of the sidewall, and wherein a portion of the strip of resilient material that is proximate the RFID tag, occupies at least part of a portion of the upstream-downstream extent of the major outward surface of the sidewall that is not occupied by the RFID tag.

Embodiment 11 is the room air purifier of any of embodiments 4-10 wherein the disposable air filter is part of an air filter assembly that is installed in the air filter receptacle of the housing, which air filter assembly comprises a prefilter that is located upstream of the disposable air filter. Embodiment 12 is the room air purifier of embodiment 11 wherein the prefilter is not permanently attached to the disposable air filter, and is reusable and washable.

Embodiment 13 is the room air purifier of any of embodiments 4-12 wherein first and second disposable air filters, each comprising at least one RFID tag that is mounted on a frame of the disposable air filter, are installed in the air filter receptacle of the housing, with the second disposable air filter being installed downstream of the first disposable air filter. Embodiment 14 is the room air purifier of any of embodiments 5-13 wherein the RFID tag is a passive, unpowered RFID tag.

Embodiment 15 is the room air purifier of any of embodiments 1-14 wherein the room air purifier further comprises at least one fine particle sensor that is located upstream of the disposable air filter when the disposable air filter is installed in the air filter receptacle.

Embodiment 16 is a remotely monitorable room air purifier system, comprising: a room air purifier comprising, a housing defining an air inlet, an air outlet, and an airflow path therethrough, wherein the housing comprises an air filter receptacle that is configured to receive at least one disposable air filter so that a filter medium of the disposable air filter is in the airflow path, an electric motor mounted within the housing and comprising a fan connected thereto, the fan positioned in the airflow path and configured to motivate air to pass through the filter medium of the disposable air filter, at least one RFID reader that is positioned and configured to read an RFID tag that is attached to the at least one disposable air filter, and to communicate information that is read from the RFID tag, to a main control unit of the room air purifier, and, a wireless communication unit that allows the main control unit of the room air purifier to communicate information that is read from the RFID tag by the RFID reader, to a portable external device; and, a portable external device that is configured to receive information communicated by the wireless communication unit of the room air purifier, such that operation of the room air purifier can be monitored by way of the portable external device.

Embodiment 17 is a remotely monitorable room air purifier system, comprising a room air purifier of any of embodiments 1-15 and comprising: a housing defining an air inlet, an air outlet, and an airflow path therethrough, wherein the housing comprises an air filter receptacle that is configured to receive at least one disposable air filter so that a filter medium of the disposable air filter is in the airflow path, an electric motor mounted within the housing and comprising a fan connected thereto, the fan positioned in the airflow path and configured to motivate air to pass through the filter medium of the disposable air filter, at least one RFID reader that is positioned and configured to read an RFID tag that is attached to the at least one disposable air filter, and to communicate information that is read from the RFID tag, to a main control unit of the room air purifier, and, a wireless communication unit that allows the main control unit of the room air purifier to communicate information that is read from the RFID tag by the RFID reader, to a portable external device; and, a portable external device that is configured to receive information communicated by the wireless communication unit of the room air purifier, such that operation of the room air purifier can be monitored by way of the portable external device.

Embodiment 18 is the remotely monitorable room air purifier system of any of embodiments 16-17 wherein the portable external device is configured to transmit information to the wireless communication unit of the room air purifier, such that operation of the room air purifier can be remotely controlled by way of the portable external device. Embodiment 19 is the remotely monitorable room air purifier system of any of embodiments 16-18, further comprising at least one disposable air filter removably installed in the air filter receptacle of the housing of the room air purifier.

Embodiment 20 is a method of operating a room air purifier, the method comprising; reading information from an RFID tag of a disposable air filter installed within a room air purifier; over a time interval during which the room air purifier is operating to purify room air, collecting a first data set indicative of the average concentration of fine particles in the air purified by the room air purifier; over the time interval, collecting a second data set indicative of the average speed with which an electric motor-driven fan of the room air purifier operates; collecting a third data set indicative of the length of the time interval; combining the first, second and third data sets into fourth, combined data set, and using the fourth data set to obtain an estimate of the usable lifetime remaining for the disposable air filter; and, wirelessly communicating the estimate of the usable lifetime of the disposable air filter to an external device, along with at least some of the information that was read from the RFID tag of the disposable air filter.

Embodiment 21 is a method of operating a room air purifier, the method comprising; reading information from an RFID tag of a disposable air filter installed within a room air purifier of any of embodiments 1-15; over a time interval during which the room air purifier is operating to purify room air, collecting a first data set indicative of the average concentration of fine particles in the air purified by the room air purifier; over the time interval, collecting a second data set indicative of the average speed with which an electric motor-driven fan of the room air purifier operates; collecting a third data set indicative of the length of the time interval; combining the first, second and third data sets into fourth, combined data set, and using the fourth data set to obtain an estimate of the usable lifetime remaining for the disposable air filter; and, wirelessly communicating the estimate of the usable lifetime of the disposable air filter to an external device, along with at least some of the information that was read from the RFID tag of the disposable air filter.

Embodiment 22 is the method of any of embodiments 20-21 wherein the wireless communicating is performed by a method chosen from the group consisting of short-range UFH radiowaves operating in a band from 2.4 to 2.485 GHz, Wi-Fi, cellular, and infrared communication. Embodiment 23 is the method of any of embodiments 20-22 wherein the RFID reader is an RFID reader/writer and the RFID tag is an RFID readable/writeable tag, and wherein method further comprises writing at least the estimate of the usable lifetime of the disposable air filter onto the RFID tag.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). To the extent that there is any conflict or discrepancy between this specification as written and the disclosure in any document that is incorporated by reference herein, this specification as written will control.

What is claimed is:

1. A room air purifier comprising:
a housing defining an air inlet, an air outlet, and an airflow path therethrough,
wherein the housing comprises an air filter receptacle that is configured to receive at least one disposable air filter so that a filter medium of the disposable air filter is in the airflow path;
an electric motor mounted within the housing and comprising a fan connected thereto, the fan positioned in the airflow path and configured to motivate air to pass through the filter medium of the disposable air filter;
at least one RFID reader that is positioned and configured to read an RFID tag that is attached to the at least one disposable air filter, and to communicate information that is read from the RFID tag, to a main control unit of the room air purifier;
a wireless communication unit that allows the main control unit of the room air purifier to communicate information that is read from the RFID tag by the RFID reader, to an external device;
and,
at least one disposable air filter removably installed in the air filter receptacle of the housing,
wherein the disposable air filter is a framed air filter that comprises at least one RFID tag that is mounted on a major outward surface of a sidewall of the frame of the disposable air filter,
and further wherein the framed, disposable air filter comprises a strip of resilient material that is attached to the major outward surface of the sidewall on which the RFID is mounted, wherein the strip extends along at least about 80% of the elongate length of the sidewall on which the RFID tag is mounted, and wherein the material of the strip protrudes further outward away from the major outward surface of the sidewall than the RFID tag protrudes, by a factor of at least about four.

2. The room air purifier of claim 1 wherein the RFID reader is remotely located from the electric motor of the room air purifier so that the RFID reader is at least 10 cm from the electric motor.

3. The room air purifier of claim 1 wherein the RFID reader is electromagnetically shielded from the electric motor of the room air purifier by at least one EMF shield that is located between the RFID reader and the electric motor.

4. The room air purifier of claim 1 wherein the RFID reader of the room air purifier is an RFID reader/writer, and wherein the RFID tag is a readable tag that stores preloaded information regarding the disposable air filter so that the preloaded information can be read by the RFID reader/writer of the room air purifier; and, wherein the RFID tag is a writeable tag that is configured to receive and store information from a main control unit of the room air purifier, by way of the RFID reader/writer.

5. The room air purifier of claim 1 wherein the RFID tag is adhesively attached to a major outward surface of the sidewall of the frame of the disposable air filter.

6. The room air purifier of claim 1 wherein the major outward surface of the sidewall exhibits an upstream-downstream extent, wherein the RFID tag occupies a portion of the upstream-downstream extent of the major outward surface of the sidewall, and wherein a portion of the strip of resilient material that is proximate the RFID tag, occupies at least part of a portion of the upstream-downstream extent of the major outward surface of the sidewall that is not occupied by the RFID tag.

7. The room air purifier of claim 1 wherein the disposable air filter is part of an air filter assembly that is installed in the air filter receptacle of the housing, which air filter assembly comprises a prefilter that is located upstream of the disposable air filter.

8. The room air purifier of claim 7 wherein the prefilter is not permanently attached to the disposable air filter, and is reusable and washable.

9. The room air purifier of claim 1 wherein first and second disposable air filters, each comprising at least one RFID tag that is mounted on a frame of the disposable air filter, are installed in the air filter receptacle of the housing, with the second disposable air filter being installed downstream of the first disposable air filter.

10. The room air purifier of claim 1 wherein the RFID tag is a passive, unpowered RFID tag.

11. The room air purifier of claim 1 wherein the room air purifier further comprises at least one fine particle sensor that is located upstream of the disposable air filter when the disposable air filter is installed in the air filter receptacle.

12. A remotely monitorable room air purifier system, comprising:
   the room air purifier and the at least one disposable air filter removably installed in the air filter receptacle of the housing of the room air purifier of claim 1, and,
   a portable external device that is configured to receive information communicated by the wireless communication unit of the room air purifier, such that operation of the room air purifier can be monitored by way of the portable external device.

13. The remotely monitorable room air purifier system of claim 12 wherein the portable external device is configured to transmit information to the wireless communication unit of the room air purifier, such that operation of the room air purifier can be remotely controlled by way of the portable external device.

14. The remotely monitorable room air purifier system of claim 12, further comprising at least one disposable air filter removably installed in the air filter receptacle of the housing of the room air purifier.

* * * * *

UNITED STATES PATENT AND TRADEMARK OFFICE
CERTIFICATE OF CORRECTION

Page 1 of 1

PATENT NO. : 10,955,150 B2
APPLICATION NO. : 16/087453
DATED : March 23, 2021
INVENTOR(S) : Andrew R. Fox It is certified that error appears in the above-identified patent and that said Letters Patent is hereby corrected as shown below:

On the Title Page

<u>Column 1, Under (Assignee)</u>
Line 1, delete "SM" and insert -- 3M --, therefor.

<u>Column 2, Under (Abstract)</u>
Lines 3 and 4, delete "A method is how to operating the room air purifier." and insert -- A method of operating the room air purifier. --, therefor.

In the Specification

<u>Column 14</u>
Line 2, delete "UFH" and insert -- UHF --, therefor.

Signed and Sealed this
Seventh Day of September, 2021

Drew Hirshfeld
*Performing the Functions and Duties of the
Under Secretary of Commerce for Intellectual Property and
Director of the United States Patent and Trademark Office*